United States Patent [19]

Fujii et al.

[11] 4,182,897
[45] Jan. 8, 1980

[54] AMINO- OR GUANIDINO-PHENYLPROPIONIC ACID DERIVATIVES

[75] Inventors: Setsuro Fujii, Toyonaka; Hiroyuki Kawamura; Seizo Taira, both of Ichikawa; Ryoji Matsui, Funabashi; Yojiro Sakurai, Kamakura; Toshiyuki Okutome, Tokyo, all of Japan

[73] Assignee: Torii & Co., Ltd., Tokyo, Japan

[21] Appl. No.: 917,232

[22] Filed: Jun. 20, 1978

[30] Foreign Application Priority Data

Jun. 24, 1977 [JP] Japan .................................. 52-75063
Jun. 24, 1977 [JP] Japan .................................. 52-75064
Apr. 14, 1978 [JP] Japan .................................. 53-44078
Apr. 14, 1978 [JP] Japan .................................. 53-44079

[51] Int. Cl.$^2$ ............... A61K 31/24; C07C 101/447; C07C 129/12
[52] U.S. Cl. ............................ 560/19; 560/34; 560/50; 424/308; 424/309
[58] Field of Search ...................... 560/19, 34, 50

[56] References Cited

U.S. PATENT DOCUMENTS

| 3,520,918 | 7/1970 | Chase et al. ............... 560/34 |
| 4,021,472 | 5/1977 | Fujii et al. ................. 560/34 |

FOREIGN PATENT DOCUMENTS

1905813  3/1970  Fed. Rep. of Germany.
47-14373  4/1972  Japan.
49-11842  1/1974  Japan .................................. 560/34

OTHER PUBLICATIONS

N. Kayama et al., Gendai Iryo, 6, 1010–1016 (1974).
P. Walsmann et al., Pharmazie, 29, H. 5, 333–336 (1974).

*Primary Examiner*—Alton D. Rollins
*Assistant Examiner*—M. C. Eakin
*Attorney, Agent, or Firm*—Beveridge, DeGrandi, Kline & Lunsford

[57] ABSTRACT

Amino- or guanidino-phenylpropionic ester derivatives represented by the formula:

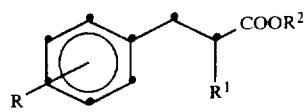

wherein R is —NH$_2$ or

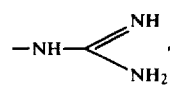

R$^1$ is hydrogen or a lower alkyl group, and R$^2$ is an unsubstituted or a lower-alkyl-, carboxyalkyl-, lower-alkoxy-, lower-alkoxycarbonyl- or halogen-substituted phenyl group or an unsubstituted or a halogen-substituted naphthyl group, and acid addition salts thereof are novel compounds exhibiting a specific enzyme-inhibitory activity to proteolytic enzymes and, therefore, they are useful as the therapeutic agent of diseases induced by abnormal activation of these enzymes. The above-mentioned compounds can be produced by subjecting a nitrocinnamic acid derivative represented by the formula:

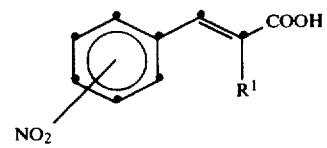

and a phenol derivative or a naphthol derivative represented by the formula:

HO—R$^2$ to an esterification in the conventional manner to obtain a nitrocinnamic ester derivative, then reducing the latter compound to obtain an aminophenylpropionic ester derivative and, if desired, reacting it with cyanamide to obtain a guanidino-phenylpropionic ester derivative and, if desired, further converting the reaction product to an acid addition salt.

30 Claims, No Drawings

AMINO- OR GUANIDINO-PHENYLPROPIONIC ACID DERIVATIVES

This invention relates to novel amino- or guanidino-phenylpropionic ester derivatives and a process for producing the same.

It has hitherto been known that guanidinocaproic acid derivatives, for example, ethyl-p-(6-guanidinohexanoyloxy) benzoate methanesulfonate (Gendai Iryo, 6, 1010–1016 (1974), Naohiro Kayama & Hiroko Yoshimura) and benzamidine derivatives, for example, 4-amidinophenylpyruvic acid (Pharmazie, 29, H. 5, 333–336 (1974), P. Walsmann, F. Markwardt, P. Richter, J. Sturzebecher, G. Wagner & H. Landmann) and the like have an inhibitory activity to proteolytic enzymes. However, the enzyme-inhibitory activity thereof is not specific but rather nonspecific in that these act on more than one proteolytic enzymes. Therefore, they have a disadvantage of inhibiting a particular enzyme causing disease as well as the other enzymes which are important for normal function of the host.

It is an object of this invention to provide novel amino- or guanidino-phenylpropionic ester derivatives.

It is another object of this invention to provide novel compounds which exhibit an enzyme-inhibitory activity to a specific proteolytic enzyme.

It is a further object of this invention to provide a process for producing the novel amino- or guanidino-phenylpropionic ester derivatives.

Other objects and advantages of this invention will become apparent from the following description.

According to this invention, there is provided an amino- or guanidino-phenylpropionic ester derivative represented by the formula (I):

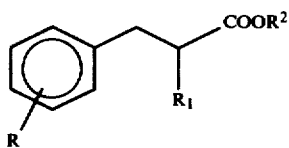

wherein R is —NH₂ or

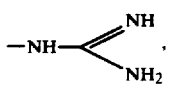

$R^1$ is hydrogen or a lower alkyl group, and $R^2$ is an unsubstituted or a lower-alkyl-, carboxyalkyl-, lower-alkoxy-, lower-alkoxycarbonyl- or halogen-substituted phenyl group or an unsubstituted or a halogen-substituted naphthyl group, or a pharmaceutically acceptable acid addition salt thereof.

The amino- or guanidino-phenylpropionic ester derivatives represented by formula (I) or their pharmaceutically acceptable acid addition salts can be produced by subjecting a nitrocinnamic acid derivative represented by formula (II):

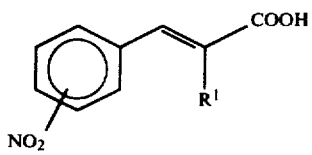

wherein $R^1$ is the same as defined above, and a phenol derivative or a naphthol derivative represented by the formula (III):

wherein $R^2$ is the same as defined above, to an esterification in the conventional manner to obtain a nitrocinnamic ester derivative represented by the formula (IV):

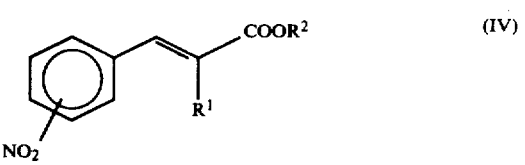

wherein $R^1$ and $R^2$ are the same as defined above, then reducing the latter derivative with a reducing catalyst to obtain an aminophenylpropionic ester derivative represented by the formula (V):

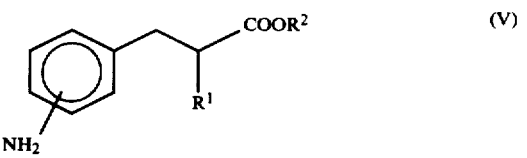

wherein $R^1$ and $R^2$ are the same as defined above, and, if desired, reacting it with cyanamide to obtain a guanidino-phenylpropionic ester derivative and, if desired, further converting the reaction product to a pharmaceutically acceptable acid addition salt.

The novel compound (I) of this invention exhibits a specific enzyme-inhibitory activity against proteolytic enzymes such as trypsin, thrombin, Cl esterase, and the like, and therefore, they are useful for the treatment of the diseases caused by activation of a particular enzyme.

In formula (I), $R^1$ is hydrogen or a lower alkyl group, preferably having 1 to 4 carbon atoms. Examples of said lower alkyl group include methyl, ethyl, n-propyl, n-butyl and the like, among which methyl, ethyl and propyl are most preferable.

In formula (I), $R^2$ is an unsubstituted or a lower-alkyl-, carboxyalkyl-, lower-alkoxy-, lower-alkoxycarbonyl- or halogen-substituted phenyl group or an unsubstituted or a halogen-substituted naphthyl group. The lower alkyl group attached to the phenyl group as its substituent has preferably 1 to 4 carbon atoms. Examples of said lower alkyl group include methyl, ethyl, n-propyl, n-butyl and the like, among which methyl and ethyl are most preferable. The alkyl group of the carboxyalkyl group attached to the phenyl group as its substituent preferably has 1 to 4 carbon atoms. Examples of said carboxyalkyl group include carboxymethyl, carboxyethyl, carboxypropyl, carboxybutyl and the like, among which carboxymethyl and carboxyethyl are most preferable. The lower alkoxy group attached to the phenyl group as its substituent has preferably 1 to 4 carbon atoms. Examples of said lower alkoxy group include methoxy, ethoxy, n-propoxy, n-butoxy and the like, among which methoxy and ethoxy are most preferable. The alkoxy group of the lower alkoxycarbonyl group attached to the phenyl group as its substituent has preferably 1 to 4 carbon atoms. Examples of said lower alkoxycarbonyl group include methoxycarbonyl, ethoxycarbonyl, n-propoxycarbonyl, n-butoxycarbonyl and the like, among which methoxycarbonyl and ethoxycarbonyl are most preferable. Examples of the halogen attached to the phenyl and naphthyl groups as their substituent include chlorine, bromine, fluorine and iodine, among which chlorine is most preferable.

Specific examples of compound (I) of this invention include the followings: p-methylphenyl β-(p-aminophenyl)-propionate, p-chlorophenyl α-methyl-β-(p-aminophenyl)-propionate, phenyl β-(p-aminophenyl)-propionate, p-methoxyphenyl α-ethyl-β-(m-aminophenyl)-propionate, p-chlorophenyl α-methyl-β-(m-aminophenyl)-propionate, p-chlorophenyl α-methyl-β-(m-aminophenyl)-propionate, p-chlorophenyl α-ethyl-β-(m-aminophenyl)-propionate, 1-naphthyl α-ethyl-β-(m-aminophenyl)-propionate, 4-chloro-1-naphthyl α-methyl-β-(m-aminophenyl)-propionate, o,o'-dimethylphenyl β-(p-aminophenyl)-propionate, p-chlorophenyl β-(p-aminophenyl)-propionate, 1-naphthyl β-(p-aminophenyl)-propionate, 2-naphthyl β-(p-aminophenyl)-propionate, p-methylphenyl α-methyl-β-(p-aminophenyl)-propionate, 1-naphthyl α-methyl-β-(p-aminophenyl)-propionate, p-chlorophenyl α-ethyl-β-(p-aminophenyl)-propionate, 1-naphthyl α-ethyl-β-(p-aminophenyl)-propionate, p-carboxymethylphenyl α-ethyl-β-(p-aminophenyl)-propionate, ethylphenyl ethylphenyl α-ethyl-β-(p-aminophenyl)-propionate, 1-naphthyl α-methyl-β-(m-aminophenyl)-propionate, p-methylphenyl α-methyl-β-(m-aminophenyl)-propionate, p-methylphenyl α-ethyl-β-(p-aminophenyl)-propionate, p-sec-butylphenyl α-ethyl-β-(p-aminophenyl)-propionate, o-methylphenyl α-ethyl-β-(p-aminophenyl)-propionate, o-bromophenyl α-ethyl-β-(p-aminophenyl)-propionate, phenyl β-(m-aminophenyl)-propionate, p-ethoxycarbonylphenyl β-(m-aminophenyl)-propionate, phenyl α-methyl-β-(m-aminophenyl)-propionate, phenyl α-ethyl-β-(m-aminophenyl)-propionate, p-ethoxycarbonylphenyl α-ethyl-β-(m-aminophenyl)-propionate, phenyl α-n-propyl-β-(m-aminophenyl)-propionate, p-ethoxycarbonylphenyl β-(p-aminophenyl)-propionate, p-methoxyphenyl β-(p-aminophenyl)-propionate, p-n-butoxyphenyl β-(p-aminophenyl)-propionate, phenyl α-methyl-β-(p-aminophenyl)-propionate, phenyl α-ethyl-β-(p-aminophenyl)-propionate, p-ethoxycarbonylphenyl α-ethyl-β-(p-aminophenyl)-propionate, p-ethoxycarbonyl-phenyl α-methyl-β-(p-aminophenyl)-propionate, p-methoxyphenyl α-methyl-β-(p-aminophenyl)-propionate, p-n-butoxycarbonylphenyl α-ethyl-β-(p-aminophenyl)-propionate, m-methoxycarbonylphenyl α-ethyl-β-(p-guanidinophenyl)-propionate, m-methoxyphenyl α-ethyl-β-(p-guanidinophenyl)-propionate, and p-methoxyphenyl α-ethyl-β-(p-guanidinophenyl)-propionate, and hydrochlorides, carbonates, methanesulfonates and tosylates of these esters.

p-chlorophenyl α-ethyl-β-(m-guanidinophenyl)-propionate, 1-naphthyl α-methyl-β-(m-guanidinophenyl)-propionate, 4-chloro-1-naphthyl α-methyl-β-(m-guanidinophenyl)-propionate, p-chlorophenyl α-methyl-β-(p-guanidinophenyl)-propionate, p-chlorophenyl α-ethyl-β-(p-guanidinophenyl)-propionate, 1-naphthyl α-methyl-β-(p-guanidinophenyl)-propionate, 1-naphthyl α-ethyl-β-(p-guanidinophenyl)-propionate, p-methylphenyl α-ethyl-β-(p-guanidinophenyl)-propionate, p-carboxymethylphenyl α-ethyl-β-(p-guanidinophenyl)-propionate, p-carboxylethylphenyl α-ethyl-β-(p-guanidinophenyl)-propionate, 1-naphthyl α-ethyl-β-(m-guanidinophenyl)-propionate, p-sec-butylphenyl α-ethyl-β-(p-guanidinophenyl)-propionate, o-methylphenyl α-ethyl-β-(p-guanidinophenyl)-propionate, o-bromophenyl α-ethyl-β-(p-guanidinophenyl)-propionate, phenyl β-(m-guanidinophenyl)-propionate, p-ethoxycarbonylphenyl β-(m-guanidinophenyl)-propionate, phenyl α-ethyl-β-(m-guanidinophenyl)-propionate, p-ethoxycarbonylphenyl α-ethyl-β-(m-guanidinophenyl)-propionate, p-methoxyphenyl α-ethyl-β-(m-guanidinophenyl)-propionate, phenyl α-n-propyl-β-(m-guanidinophenyl)-propionate, phenyl β-(p-guanidinophenyl)-propionate, p-methoxyphenyl β-(p-guanidinophenyl)-propionate, p-n-butoxyphenyl β-(p-guanidinophenyl)-propionate, phenyl α-methyl-β-(p-guanidinophenyl)-propionate, phenyl α-ethylβ-(p-guanidinophenyl)-propionate, p-ethoxycarbonylphenyl α-ethyl-β-(p-guanidinophenyl)-propionate, p-ethoxycarbonyl-phenyl α-methyl-β-(p-guanidinophenyl)-propionate, p-methoxyphenyl α-methyl-β-(p-guanidinophenyl)-propionate, p-n-butoxycarbonylphenyl α-ethyl-β-(p-guanidinophenyl)-propionate, m-methoxycarbonylphenyl α-ethyl-β-(p-guanidinophenyl)-propionate, m-methoxyphenyl α-ethyl-β-(p-guanidinophenyl)-propionate, and p-methoxyphenyl α-ethyl-β-(p-guanidinophenyl)-propionate, and hydrochlorides, carbonates, methanesulfonates and tosylates of these esters.

According to the process of this invention, the compound of formula (I) can be produced by subjecting a nitrocinnamic acid derivative represented by formula (II) and a phenol derivative or a naphthol derivative represented by formula (III) to an esterification in the conventional manner to obtain a nitrocinnamic ester derivative represented by formula (IV), then reducing the ester derivative and, if desired, reacting it with cyanamide to obtain a guanidinophenylpropionic ester derivative. Said esterification can be effected by a conventional well-known process such as a DCC (dicyclohexylcarbodiimide) process, a DPPA (diphenylphosphoryl azide) process, a mixed acid anhydride process, an acid chloride process and the like. However, the acid chloride process is most preferable among these processes from the viewpoint of easiness of procedure, economy and product purity. The acid chloride process can be carried out advantageously in the presence of a dehydrohalogenating agent such as an organic base, for example, triethylamine, tributylamine, pyridine or the like or an inorganic base, for example, potassium carbonate, sodium carbonate or the like, because a hydrogen halide is formed as a by-product in the acid chloride process. This reaction is carried out in a solvent. Preferable solvents usable are benzene, ethyl acetate, diethyl ether, tetrahydrofuran, pyridine and the like, among which ethyl acetate is most preferable from the viewpoint of product purity. The esterification proceeds relatively readily in a wide temperature range. In general, the reaction is completed in a period of 30 minutes to 1 hour at a temperature of 0° to 30° C.

The nitrocinnamic acid derivatives represented by formula (II) used in this invention can be synthesized by reacting nitrobenzaldehyde with an anhydride or ester of a lower fatty acid such as acetic anhydride, propionic anhydride, lactic anhydride, methyl acetate or the like under the conditions adopted in the reactions well-known in the name of Perkin reaction or Claisen condensation reaction.

Examples of the nitrocinnamic acid derivatives of formula (II) include p- and m-nitrocinnamic acids, p- and m-nitro-α-methylcinnamic acids, p- and m-nitro-α-ethylcinnamic acids, p- and m-nitro-α-n-propylcinnamic acids, p- and m-nitro-α-n-butylcinnamic acids and the like.

Examples of the phenol derivatives and naphthol derivatives represented by formula (III) include phenol, p-methylphenol, p-ethylphenol, p-n-propylphenol, p-n-butylphenol, p-chlorophenol, p-bromophenol, o,o'-dimethylphenol, p-methoxyphenol, p-ethoxyphenol, p-n-butoxyphenol, p-methoxycarbonylphenol, p-ethoxycarbonylphenol, p-n-butoxycarbonylphenol, p-carboxymethylphenol, p-carboxyethylphenol, naphthol, monocloronaphthol and the like.

Reduction of the nitrocinnamic ester derivatives of formula (IV) can preferably be effected with a catalyst employed in the usual catalytic reduction, such as palladium-carbon, Raney nickel, platinum oxide and the like. That is to say, a nitrocinnamic ester derivative of formula (IV) is dissolved or suspended in an organic solvent and gaseous hydrogen is introduced thereinto in the presence of the above-mentioned catalyst, whereby an aminophenylpropionic acid derivative represented by formula (I), wherein R is —NH₂, can readily be produced. Preferable solvents usable in this reaction are methanol, ethanol, dimethylformamide, tetrahydrofuran, diethyl ether and the like, among which methanol and ethanol are particularly preferable. The reduction can proceed relatively readily in a wide temperature range. In general, the reduction is completed in a period of 1 to 2 hours at a temperature of 20° to 40° C.

The aminophenylpropionic ester derivative of formula (I) wherein R is —NH₂ can be isolated from the reaction mixture in a conventional manner. That is, it can be isolated by removing the catalyst from the reaction mixture by filtration and then concentrating the filtrate under reduced pressure.

When it is desired to obtain an acid addition salt of the aminophenylpropionic ester derivative the isolated derivative is dissolved in diethyl ether and an acid corresponding to the desired salt is added to the resulting solution, whereby the derivative can be converted into an acid addition salt at room temperature.

When it is desired to produce a guanidinophenylpropionic ester derivative from the aminophenylpropionic ester derivative, the isolated aminophenylpropionic ester derivative is dissolved or suspended in an organic solvent and then reacted with cyanamide, or alternatively, the isolated aminophenylpropionic ester derivative is directly reacted with cyanamide, or alternatively, the aminophenylpropionic ester derivative, without isolation from the reaction mixture, is subjected to reaction with cyanamide, whereby the intended guanidinophenylpropionic ester derivative represented by formula (I), wherein R is

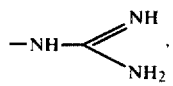

can be obtained. The preferable solvents usable in the above reaction include methanol, ethanol, dimethylformamide, tetrahydrofuran, diethyl ether and the like, among which methanol and ethanol are preferable. The reaction proceeds readily at a temperature ranging from room temperature to the boiling point of the solvent used. The objective guanidinophenylpropionic ester derivative can be isolated from the reaction mixture in the conventional manner. That is, it can readily be isolated by concentrating the reaction mixture under reduced pressure and recrystallizing the residue from an appropriate solvent.

When it is desired to obtain a carbonate of the guanidinophenylpropionic ester derivative, the isolated derivative is added to saturated aqueous sodium bicarbonate solution. When it is desired to obtain other salts, the carbonate is suspended in ethyl alcohol and an acid corresponding to the desired salt is added to the resulting suspension, thereby obtaining the desired salt.

The acid addition salts of the compound of formula (I) include carbonate, hydrochloride, hydrobromide, sulfate, phosphate, nitrate, acetate, lactate, oxalate, maleate, fumalate, tartarate, citrate, ascorbate, benzenesulfonate, toluenesulfonate, methanesulfonate and the like.

The compounds of formula (I) of this invention are new type inhibitors for trypsin, Cl esterase or thrombin possessing a very high specificity. They also have an intense inhibitory action on the platelet aggregation.

The synthetic inhibitors against these enzymes that have hitherto been known are guanidinocaproic acid derivatives such as FOY, namely ethyl p-(6-guanidinohexanoyloxy)benzoate methanesulfonate [Gendai Iryo, 6, 1010–1016 (1974), Naohiro Kayama and Hiroko Yoshimura] and benzamidine derivatives such as 4-amidinophenylpyruvic acid [Pharmazie, 29, H. 5, 333–336 (1974), P. Walsmann, F. Markwardt, P. Richter, J. Sturzebecher, G. Wagner and H. Landmann]. However, all these compounds are low in specificity and generally exhibit a broad spectrum of inhibitory activity. As a platelet-aggregation-inhibiting agent, there have been known non-steroidal antiinflammatory drugs such as aspirin. However, the compounds of this invention are much superior to them in the inhibitory action. Of the compounds of this invention a compound having an antithrombin activity or a platelet-aggregation inhibiting activity is useful for the treatment of thromobosis. A compound having a Cl-esterase-inhibiting activity is useful for the treatment of diseases caused by antigen-antibody reaction such as the autoimmune disease. A compound having an anti-trypsin activity is useful for the treatment of acute pancreatitis.

This invention is explained below in more detail by reference to Examples which are not by way of limitation but only by way of illustration. In the Examples, percentages are by weight unless otherwise specified.

EXAMPLE 1 p-Methylphenyl β-(p-aminophenyl)-propionate hydrochloride (Compound No. 1)

Phosphorus pentachloride (22 g) was added to 19.3 g of p-nitrocinnamic acid suspended in 300 ml of ethyl acetate, and the resulting suspension was stirred at room temperature for 1 hour. After the reaction, the solvent was removed by distillation under reduced pressure. The resulting precipitates of p-nitrocinnamoyl chloride were dissolved in 300 ml of ethyl acetate and 10.8 g of p-methylphenol was added to the resulting solution, after which 12 g of triethylamine was slowly added thereto at room temperature with constant stirring. After the mixture was subjected to reaction at room temperature for 1 hour, the reaction mixture was washed with 10% HCl, 10% NaOH and water in this order and dried on anhydrous magnesium sulfate. Then the solvent was removed by distillation under reduced pressure, whereby p-methylphenyl p-nitrocinnamate was obtained. Yield: 26.8 g (95%); melting point: 168°–170° C.; IR (cm$^{-1}$): 1720, 1510, 1345. HCl).

In 200 ml of ethanol were suspended 26.8 g of the p-methylphenyl p-nitrocinnamate thus obtained and 2.0 g of 10% palladium-carbon, into which gaseous hydrogen was introduced with stirring. Thus, about 8.5 liters of hydrogen was absorbed in 2 hours. After the reaction, the palladium catalyst was removed by filtration and the solvent was then removed by distillation under reduced pressure. The residue was dissolved in 200 ml of diethyl ether, and gaseous hydrogen chloride was introduced into the resulting solution, upon which p-methylphenyl p-aminophenylpropionate hydrochloride precipitated in the form of colorless crystals. Yield: 24.2 g (87.7%); melting point: 203°–205° C. (decomposed); IR (cm$^{-1}$): 3250–2500, 1745, 1506; MS: M$^+$=m/e 255 (M.W. - HCl).

Elementary analysis (as $C_{16}H_{18}NO_2Cl = 291.77$) Calcd.: C, 65.86%; H, 6.22%; N, 4.80%; Found: C, 65.96%; H, 6.33%; N, 4.76%.

This compound inhibited the tosylarginine methyl ester hydrolyzing action of thrombin in vitro. The concentration at which said compound inhibited said hydrolysis by 50% (ID$_{50}$) was $8.8 \times 10^{-4}$ M.

EXAMPLE 2 p-Chlorophenyl α-methyl-β-(p-aminophenyl)-propionate hydrochloride (Compound No. 2)

Phosphorus pentachloride (22 g) was added to 20.7 g of p-nitro-α-methylcinnamic acid suspended in 300 ml of ethyl acetate, and the resulting mixture was stirred at room temperature for 1 hour. After the reaction, the solvent was removed by distillation under reduced pressure. The resulting precipitates of p-nitro-α-methylcinnamoyl chloride were dissolved in 300 ml of ethyl acetate, and 12.5 g of p-chlorophenol was added to the resulting solution. The resulting mixture was subjected to reaction at room temperature for 1 hour. Then the reaction mixture was washed with 10% HCl, 10% NaOH and water in this order, and dried on anhydrous magnesium sulfate, after which the solvent was distilled off under reduced pressure, to obtain p-chlorophenyl p-nitro-α-methylcinnamate. Yield: 29.8 g (93.9%); melting point: 111°–112° C.; IR (cm$^{-1}$): 1721, 1512, 1342.

In 250 ml of ethanol were suspended 29.8 g of the p-chlorophenyl p-nitro-α-methylcinnamate thus obtained and 3.0 g of 10% palladium-carbon, and gaseous hydrogen was introduced into the resulting suspension with stirring. Thus, about 8.5 liters of hydrogen was absorbed in 2 hours. After the reaction, the palladium catalyst was removed by filtration and the solvent was then distilled off under reduced pressure. The residue was dissolved in 200 ml of diethyl ether, and gaseous hydrogen chloride was introduced into the resulting solution, upon which p-chlorophenyl α-methyl-β-(p-aminophenyl)-propionate hydrochloride precipitated in the form of colorless crystals. Yield: 24.8 g (81.0%); melting point: 216°–218° C.; IR (cm$^{-1}$); 3250–2500, 1741, 1510, 1198; MS: M$^+$=m/e 289, 291 (M.W. - HCl).

Elementary analysis (as $C_{16}H_{17}NO_2Cl_2 = 326.23$) Calcd.: C, 58.90%; H, 5.25%; N, 4.29%; Found: C, 58.62%; H, 5.10%; N, 4.21%.

In vitro, this compound inhibited the tosylarginine methyl ester hydrolyzing action of trypsin. The ID$_{50}$ of this compound was $3.3 \times 10^{-4}$ M.

EXAMPLE 3

Phenyl β-(p-aminophenyl)-propionate hydrochloride (Compound No. 3)

Phosphorus pentachloride (22 g) was added to 19.3 g of p-nitrocinnamic acid suspended in 300 ml of ethyl acetate, and the resulting mixture was stirred at room temperature for 1 hour. After the reaction, the solvent was distilled off under reduced pressure, upon which p-nitrocinnamoyl chloride precipitated. The precipitates thus obtained were dissolved in 300 ml of ethyl acetate, and 9.4 g of phenol was added to the resulting solution, after which 12 g of triethylamine was slowly added thereto at room temperature with stirring. After reaction at room temperature for 1 hour, the reaction mixture was washed with 10% HCl, 10% NaOH and water in this order and dried on anhydrous magnesium sulfate. The solvent was then distilled off under reduced pressure, to obtain phenyl p-nitrocinnamate. Yield: 25.5 g (95%); melting point: 151°–152° C.; IR (cm$^{-1}$): 1720, 1529, 1345.

In 200 ml of ethanol were suspended 25.5 g of the phenyl p-nitrocinnamate thus obtained and 2.0 g of 10% palladium-carbon, and gaseous hydrogen was introduced with stirring into the suspension. About 8.5 liters of hydrogen was absorbed in 2 hours. After the reaction, the palladium catalyst was filtered off and the solvent was distilled off under reduced pressure. The residue was dissolved in 200 ml of diethyl ether,, and gaseous hydrogen chloride was introduced into the resulting solution, upon which phenyl p-aminophenylpropionate hydrochloride precipitated in the form of colorless crystals. Yield: 23.7 g (89.9%); melting point: 240° C. (decomposed); IR (cm$^{-1}$): 3250–2500, 1742, 1511; MS: M$^+$=m/e 241 (M.W. - HCl).

Elementary analysis (as $C_{15}H_{16}NO_2Cl = 277.75$) Calcd.: C, 64.86%; H, 5.81%; N, 5.04%; Found: C, 64.64%; H, 5.89%; N, 5.01%.

In vitro, this compound inhibited the tosylarginine methyl ester hydrolyzing action of thrombin. The ID$_{50}$ of this compound was $2.9 \times 10^{-4}$ M. However, it had no inhibitory action on trypsin, plasmin, Cl esterase and kallikrein.

EXAMPLE 4 p-Methoxyphenyl α-ethyl-β-(m-aminophenyl)-propionate hydrochloride (Compound No. 4)

Phosphorus pentachloride (22 g) was added to 22.1 g of m-nitro-α-ethylcinnamic acid suspended in 300 ml of ethyl acetate, and the mixture was stirred at room temperature for 1 hour. After the reaction, the solvent was distilled off under reduced pressure, upon which m-nitro-α-ethylcinnamoyl chloride precipitated. This compound was dissolved in 300 ml of ethyl acetate, and 12.4 g of p-methoxyphenol was added thereto. After the reaction at room temperature for 1 hour, the reaction mixture was washed with 10% HCl, 10% NaOH and water in this order and dried on anhydrous magnesium sulfate. The solvent was then distilled off under reduced pressure to obtain p-methoxyphenyl m-nitro-α-ethylcinnamate. Yield: 30.7 g (93.9%); melting point: 65°–66° C.; IR (cm$^{-1}$): 1710, 1503, 1351.

In 250 ml of ethanol were suspended 30.7 g of the p-methoxyphenyl m-nitro-α-ethylcinnamate thus obtained and 3.0 g of 10% palladium-carbon, and gaseous hydrogen was introduced into the resulting suspension wth stirring. About 8.5 liters of hydrogen was absorbed in 2 hours. After the reaction, the palladium catalyst was filtered off and the solvent was distilled off under reduced pressure. The residue was dissolved in 200 ml of diethyl ether, and gaseous hydrogen chloride was introduced into the resulting solution, upon which p-methoxyphenyl α-ethyl-β-(m-aminophenyl)-propionate hydrochloride precipitated in the form of colorless crystals. Yield: 29.0 g (86.4%); melting point: 110°–111° C.; IR (cm$^{-1}$): 3250–2500, 1738, 1503; MS: M$^+$ = m/e 319 (M.W. - HCl).

In vitro, this compound inhibited the tosylarginine methyl ester hydrolyzing action of tryspin. The ID$_{50}$ of this compound was $4.0 \times 10^{-4}$ M. However, it had no inhibitory action on plasmin, Cl esterase, kallikrein and thrombin.

EXAMPLE 5

The compounds of Table 1 were synthesized following the above-mentioned procedure, except that the starting materials were different in R$^1$ and R$^2$.

Table 1

| Compound No. | Position of —NH$_2$ | R$^1$ | R$^2$ | Salt | Melting point (°C.) | Molecular formula | Calculated (%) C | H | N | Found (%) C | H | N |
|---|---|---|---|---|---|---|---|---|---|---|---|---|
| 5 | m | CH$_3$ |  | HCl | 85–90 | C$_{16}$H$_{17}$NO$_2$Cl$_2$ | 58.90 | 5.25 | 4.29 | 58.27 | 5.33 | 4.35 |
| 6 | m | CH$_2$CH$_3$ |  | HCl | 147–148 | C$_{17}$H$_{19}$NO$_2$Cl$_2$ | 60.01 | 5.63 | 4.12 | 60.13 | 5.48 | 4.27 |
| 7 | m | CH$_2$CH$_3$ |  | HCl | 122–124 | C$_{21}$H$_{22}$NO$_2$Cl | 70.87 | 6.23 | 3.94 | 70.99 | 6.15 | 3.98 |
| 8 | m | CH$_3$ |  | HCl | 115–117 | C$_{20}$H$_{19}$NO$_2$Cl$_2$ | 63.84 | 5.09 | 3.72 | 63.71 | 5.27 | 3.71 |
| 9 | p | H |  | HCl | 148–149 | C$_{27}$H$_{20}$NO$_2$Cl | 66.77 | 6.59 | 4.58 | 67.02 | 6.44 | 4.46 |
| 10 | p | H |  | HCl | 200 | C$_{15}$H$_{15}$NO$_2$Cl$_2$ | 57.70 | 4.84 | 4.49 | 57.99 | 4.69 | 4.31 |
| 11 | p | H |  | HCl | 211–213 | C$_{19}$H$_{18}$NO$_2$Cl | 69.61 | 5.54 | 4.27 | 69.55 | 5.29 | 4.39 |
| 12 | p | H |  | HCl | 165–167 | C$_{19}$H$_{18}$NO$_2$Cl | 69.61 | 5.54 | 4.27 | 69.98 | 5.64 | 4.77 |
| 13 | p | CH$_3$ |  | HCl | 194–195 | C$_{17}$H$_{20}$NO$_2$Cl | 66.77 | 6.59 | 4.58 | 67.03 | 6.22 | 4.17 |
| 14 | p | CH$_3$ |  | HCl | 223–225 | C$_{20}$H$_{20}$NO$_2$Cl | 70.27 | 5.90 | 4.10 | 69.96 | 6.32 | 3.98 |
| 15 | p | CH$_2$CH$_3$ |  | HCl | 179–181 | C$_{17}$H$_{19}$NO$_2$Cl$_2$ | 60.01 | 5.63 | 4.12 | 60.57 | 5.49 | 4.00 |
| 16 | p | CH$_2$CH$_3$ |  | HCl | 198–200 | C$_{21}$H$_{22}$NO$_2$Cl | 70.87 | 6.23 | 3.94 | 70.74 | 6.10 | 3.77 |
| 17 | p | CH$_2$CH$_3$ | —⟨O⟩—CH$_2$COOH | HCl | 130 | C$_{19}$H$_{22}$NO$_4$Cl | 62.72 | 6.10 | 3.85 | 61.96 | 5.89 | 3.58 |

Table 1-continued

Structure: benzene ring with NH2 substituent and CH2-CH(R1)-COO-R2 side chain

| Compound No. | Position of -NH2 | R1 | R2 | Salt | Melting point (°C.) | Molecular formula | Calculated (%) C | H | N | Found (%) C | H | N |
|---|---|---|---|---|---|---|---|---|---|---|---|---|
| 18 | p | $CH_2CH_3$ | -Ph-$CH_2CH_2COOH$ | HCl | Oil | $C_{20}H_{24}NO_4Cl$ | 63.57 | 6.40 | 3.71 | 63.19 | 6.71 | 3.56 |
| 19 | m | $CH_3$ | naphthyl | HCl | Oil | $C_{20}H_{20}NO_2Cl$ | 70.27 | 5.90 | 4.10 | 70.01 | 6.41 | 3.92 |
| 20 | m | $CH_3$ | -Ph-$CH_3$ | HCl | Oil | $C_{17}H_{20}NO_2Cl$ | 66.77 | 6.59 | 4.58 | 66.33 | 6.87 | 4.31 |
| 21 | p | $CH_2CH_3$ | -Ph-$CH_3$ | HCl | 169–170 | $C_{18}H_{22}NO_2Cl$ | 67.59 | 6.93 | 4.38 | 67.46 | 6.85 | 4.40 |
| 22 | p | $CH_2CH_3$ | -Ph-CH($CH_3$)$CH_2CH_3$ | HCl | Oil | $C_{21}H_{28}NO_2Cl$ | 69.69 | 7.80 | 3.87 | 69.14 | 7.60 | 3.99 |
| 23 | p | $CH_2CH_3$ | $H_3C$-Ph- | HCl | 188–189 | $C_{18}H_{22}NO_2Cl$ | 67.59 | 6.93 | 4.38 | 67.21 | 6.97 | 4.01 |
| 24 | p | $CH_2CH_3$ | Br-Ph- | HCl | 212–213 | $C_{17}H_{19}NO_2BrCl$ | 53.07 | 4.98 | 3.64 | 53.02 | 4.82 | 3.82 |
| 25 | m | H | -Ph | HCl | 163–166 | $C_{15}H_{16}NO_2Cl$ | 64.86 | 5.81 | 5.04 | 64.57 | 5.98 | 5.26 |
| 26 | m | H | -Ph-$COOC_2H_5$ | HCl | 140–142 | $C_{18}H_{20}NO_4Cl$ | 61.80 | 5.76 | 4.00 | 61.38 | 5.68 | 4.10 |
| 27 | m | $CH_3$ | -Ph | HCl | Oil | $C_{16}H_{18}NO_2Cl$ | 65.86 | 6.22 | 4.80 | 65.71 | 6.11 | 4.92 |
| 28 | m | $CH_2CH_3$ | -Ph | HCl | 83–85 | $C_{17}H_{20}NO_2Cl$ | 66.77 | 6.59 | 4.58 | 66.36 | 6.84 | 4.77 |
| 29 | m | $CH_2CH_3$ | -Ph-$COOC_2H_5$ | HCl | 130–131 | $C_{20}H_{24}NO_4Cl$ | 63.57 | 6.40 | 3.71 | 63.36 | 6.74 | 3.61 |
| 30 | m | $CH_2CH_2CH_3$ | -Ph | HCl | 72–74 | $C_{18}H_{22}NO_2Cl$ | 67.59 | 6.93 | 4.38 | 67.58 | 6.91 | 4.59 |
| 31 | p | H | -Ph-$COOC_2H_5$ | HCl | 206–207 | $C_{18}H_{20}NO_4Cl$ | 61.80 | 5.76 | 4.00 | 61.49 | 5.53 | 4.24 |
| 32 | p | H | -Ph-$OCH_3$ | free | 84–85 | $C_{16}H_{17}NO_3$ | 70.83 | 6.32 | 5.16 | 70.61 | 6.10 | 5.22 |
| 33 | p | H | -Ph-$O(CH_2)_3CH_3$ | HCl | 208–210 | $C_{19}H_{24}NO_3Cl$ | 65.23 | 6.91 | 4.00 | 65.13 | 6.77 | 4.01 |
| 34 | p | $CH_3$ | -Ph | HCl | 165–170 | $C_{16}H_{18}NO_2Cl$ | 65.91 | 6.22 | 4.80 | 65.98 | 6.02 | 4.76 |
| 35 | p | $CH_2CH_3$ | -Ph | HCl | 190–195 | $C_{17}H_{20}NO_2Cl$ | 66.77 | 6.59 | 4.24 | 66.15 | 6.49 | 4.16 |
| 36 | p | $CH_2CH_3$ | -Ph-$COOC_2H_5$ | HCl | 153–154 | $C_{20}H_{24}NO_4Cl$ | 63.57 | 6.40 | 3.71 | 63.87 | 6.93 | 3.85 |
| 37 | p | $CH_3$ | -Ph-$COOC_2H_5$ | HCl | 152–156 | $C_{19}H_{22}NO_4Cl$ | 62.72 | 6.10 | 3.85 | 62.81 | 6.00 | 3.96 |
| 38 | p | $CH_3$ | -Ph-$OCH_3$ | HCl | 149–152 | $C_{17}H_{20}NO_3Cl$ | 63.45 | 6.26 | 4.35 | 63.73 | 6.02 | 4.08 |

Table 1-continued

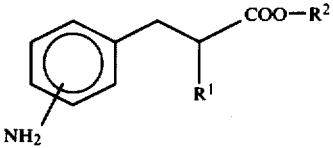

| Compound No. | Position of —NH₂ | $R^1$ | $R^2$ | Salt | Melting point (°C.) | Molecular formula | Calculated (%) C | Calculated (%) H | Calculated (%) N | Found (%) C | Found (%) H | Found (%) N |
|---|---|---|---|---|---|---|---|---|---|---|---|---|
| 39 | p | H | 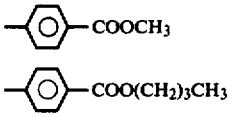 —COOCH₃ | HCl | 111–112 | $C_{17}H_{18}NO_4Cl$ | 60.80 | 5.40 | 4.17 | 60.58 | 5.33 | 4.17 |
| 40 | p | $CH_2CH_3$ | 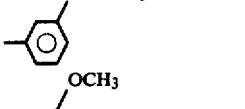 —COO(CH₂)₃CH₃ | HCl | 92–93 | $C_{22}H_{28}NO_4Cl$ | 65.09 | 6.95 | 3.45 | 64.81 | 6.94 | 3.35 |
| 41 | p | $CH_2CH_3$ | COOCH₃ 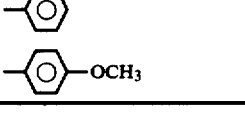 | HCl | 181–184 | $C_{19}H_{22}NO_4Cl$ | 62.72 | 6.10 | 3.85 | 62.97 | 6.10 | 3.76 |
| 42 | p | $CH_2CH_3$ | OCH₃ 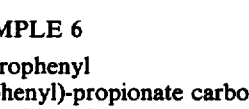 | HCl | 166–167 | $C_{18}H_{22}NO_3Cl$ | 64.37 | 6.60 | 4.17 | 64.45 | 6.76 | 4.30 |
| 43 | p | $CH_2CH_3$ | —OCH₃ | HCl | 167–168 | $C_{18}H_{22}NO_3Cl$ | 64.37 | 6.60 | 4.17 | 64.12 | 6.37 | 4.03 |

EXAMPLE 6 p-Chlorophenyl α-methyl-β-(m-guanidinophenyl)-propionate carbonate (Compound No. 44)

Phosphorus pentachloride (22 g) was added to 20.7 g of m-nitro-α-methylcinnamic acid suspended in 300 ml of ethyl acetate, and the resulting mixture was stirred at room temperature for 1 hour. After the reaction, the solvent was removed by distillation under reduced pressure, upon which m-nitro-α-methylcinnamoyl chloride precipitated. This compound was dissolved in 300 ml of ethyl acetate, and 12.9 g of p-chlorophenol was added thereto, after which the resulting solution was subjected to reaction at room temperature for 1 hour. Then the reaction mixture was washed with 10% HCl, 10% NaOH and water in this order and dried on anhydrous magnesium sulfate. The solvent was thereafter distilled off under reduced pressure to obtain p-chlorophenyl m-nitro-α-methylcinnamate in a crystalline form. Yield: 28.5 g (89.9%); melting point: 102° C.; IR (cm⁻¹): 1727, 1528, 1352.

In 250 ml of ethanol were suspended 28.5 g of the p-chlorophenyl m-nitro-α-methylcinnamate thus obtained and 3.0 g of 10% palladium-carbon, and gaseous hydrogen was introduced into the resulting suspension with stirring. About 8.5 liters of hydrogen was absorbed in 2 hours. After the reaction, the palladium catalyst was filtered off and the solvent was removed by distillation under reduced pressure. The residue was dissolved in 200 ml of ethyl ether, and gaseous hydrogen chloride was introduced into the resulting solution to obtain p-chlorophenyl α-methyl-β-(m-aminophenyl)-propionate hydrochloride in the form of colorless crystals. Yield: 23.0 g (78.5%); melting point: 85°–95° C.; IR (cm⁻¹): 3500–2500, 1748, 1492.

In 200 ml of ethanol were dissolved 23.0 g of the p-chlorophenyl α-methyl-β-(m-aminophenyl)-propionate hydrochloride thus obtained and 4.2 g of cyanamide, and the resulting solution was subjected to reaction at 70° C. for 5 hours. After the reaction, the solvent was removed by distillation under reduced pressure, to obtain p-chlorophenyl α-methyl-β-(m-guanidinophenyl)-propionate hydrochloride in the form of an oily matter. This compound was dissolved in 50 ml of ethanol, and then added to saturated aqueous NaHCO₃ solution, upon which colorless crystals precipitated. The crystals were collected by filtration and washed with water and acetone, to obtain p-chlorophenyl α-methyl-β-(m-guanidinophenyl)-propionate carbonate. Yield: 19.4 g (70%); melting point: 87°–90° C.; IR (cm⁻¹); 3500–2500, 1748, 1660, 1490; MS: M⁺ = m/e 331 (M.W. - H₂CO₃).

Elementary analysis (as $C_{18}H_{20}N_3O_5Cl = 393.83$) Calcd.: C; 54.89% H; 5.12%; N; 10.67%; Found:: C; 54.55%; H; 5.33%; N; 10.54%.

In vitro, this compound inhibited the acetyltyrosine ethyl ester hydrolyzing action of Cl esterase. The ID₅₀ of this compound was $2.5 \times 10^{-4}$ M.

EXAMPLE 7 p-Methylphenyl α-methyl-β-(p-guanidinophenyl)-propionate hydrochloride (Compound No. 45)

Phosphorus pentachloride (22 g) was added to 20.7 g of p-nitro-α-methylcinnamic acid suspended in 300 ml of ethyl acetate, and the resulting mixture was stirred at room temperature for 1 hour. After the reaction, the solvent was removed by distillation under reduced pressure, upon which p-nitro-α-methylcinnamoyl chloride precipitated. This compund was dissolved in 300 ml of ethyl acetate, and 10.8 g of p-methyl phenol was added to the solution, to which 12 g of triethylamine was then slowly added at room temperature with stirring. The resulting mixture was subjected to reaction at room temperature for 1 hour. Then, 50 ml of 10% HCl was added, and the thus precipitated p-methylphenyl p-nitro-α-methylcinnamate was collected by filtration. Yield: 26.4 g (89%); melting point: 125°–126° C.; IR (cm⁻¹): 1710, 1502, 1338.

In 200 ml of ethanol were suspended 26.4 g of the p-methylphenyl p-nitro-α-methylcinnamate thus obtained and 2.0 g of 10% palladium-carbon, and gaseous hydrogen was introduced into the suspension with stirring. About 8.5 liters of hydrogen was absorbed in 2 hours. After the reaction, the palladium catalyst was filtered off and the solvent was removed by distillation under reduced pressure. The residue was dissolved in 200 ml of diethyl ether, and gaseous hydrogen chloride was introduced into the resulting solution, upon which p-methylphenyl α-methyl-β-(p-aminophenyl)-propionate hydrochloride precipitated in the form of colorless crystals. Yield: 21.8 g (80%); melting point: 194°-195° C.; IR (cm$^{-1}$): 3250-2500, 1741, 1200.

In 200 ml of ethanol were dissolved 21.8 g of the p-methylphenyl α-methyl-β-(p-aminophenyl)-propionate hydrochloride obtained and 4.2 of cyanamide, and the resulting solution was subjected to reaction at 70° C. for 5 hours. After the reaction, the solvent was removed by distillation under reduced pressure, to obtain an oily product. A mixture of ethanol and diethyl ether was added thereto and the solution was cooled, upon which crystals precipitated. The crystals were collected by filtration and recrystallized from an ethanol-diethyl ether mixture, to obtain p-methylphenyl α-methyl-β-(p-guanidinophenyl)propionate hydrochloride in the form of colorless crystals. Yield: 17.4 g (70%); melting point: 146°-148° C.; IR (cm$^{-1}$): 3500-2550, 1748, 1653, 1631; MS: M+ =m/e 312 (M.W. -HCl).

Elementary analysis (as $C_{18}H_{22}N_3O_2Cl = 347.84$) Calcd.: C, 62.15%; H, 6.38%; N, 12.08%; Found: C, 62.16%; H, 6.45%; N, 12.38%.

In vitro, this compound inhibited the acetyltyrosine ethyl ester hydrolyzing action of Cl esterase. The $ID_{50}$ of this compound was $7.8 \times 10^{-4}$ M.

EXAMPLE 8

Phenyl α-methyl-β-(m-guanidinophenyl)-propionate carbonate (Compound No. 46).

Phosphorus pentachloride (22 g) was added to 20.7 g of m-nitro-α-methylcinnamic acid suspended in 300 ml of ethyl acetate, and the resulting mixture was stirred at room temperature for 1 hour. After the reaction, the solvent was removed by distillation under reduced pressure, upon which m-nitro-α-methylcinnamoyl chloride precipitated. This was dissolved in 300 ml of ethyl acetate, and 9.4 g of phenol was added to the solution. The solution was subjected to reaction at room temperature for 1 hour. Then the reaction mixture was washed with 10% HCL, 10% NaOH and water in this order and dried on anhydrous magnesium sulfate. The solvent was distilled off under reduced pressure, to obtain phenyl m-nitro-α-methylcinnamate in the form of a light yellow oily matter. Yield: 25.5 g (90%); IR (cm$^{-1}$); 1720, 1525, 1352.

In 250 ml of ethanol were suspended 25.5 g of the phenyl m-nitro-α-methylcinnamate obtained and 3.0 g of 10% palladium-carbon, and gaseous hydrogen was introduced into the resulting suspension with stirring. About 8.5 liters of hydrogen was absorbed in 2 hours. After the reaction, the palladium catalyst was filtered off and the solvent was removed by distillation under reduced pressure. The residue was dissolved in 200 ml of diethyl ether, and gaseous hydrogen chloride was introduced into the solution, to obtain phenyl α-methyl-β-(m-aminophenyl)-propionate hydrochloride in the form of a colorless oily matter. Yield: 24.3 g (93%); IR (cm$^{-1}$): 3500-2500, 1730, 1490.

In 200 ml of ethanol were dissolved 24.3 g of the phenyl α-methyl-β-(m-aminophenyl)-propionate hydrochloride obtained and 4.2 g of cyanamide, and the solution was subjected to reaction at 70° C. for 5 hours. After the reaction, the solvent was removed by distillation under reduced pressure to obtain phenyl α-methyl-β-(m-guanidinophenyl)-propionate hydrochloride in the form of an oily matter. This was dissolved in 50 ml of ethanol and then added to saturated aqueous NaHCO$_3$ solution, upon which colorless crystals precipitated. The crystals were collected by filtration and washed with water and acetone, to obtain phenyl α-methyl-β-(m-guanidinophenyl)-propionate carbonate. Yield: 22.6 g (75%); melting point: 97°-98° C.; IR (cm$^{-1}$): 3500-2500, 1745, 1682, 1625; MS: M+=m/e 297 (M.W.-H$_2$CO$_3$).

Elementary analysis: (as $C_{18}H_{21}N_3O_5 = 359.37$) Calcd.: C, 60.16%; H, 5.89%; N, 11.69%; Found: C, 60.30%; H, 6.38%; N, 11.75%.

In vitro, this compound inhibited the acetyltyrosine ethyl ester hydrolzing action of Cl esterase. The $ID_{50}$ of this compound was $3.1 \times 10^{-4}$ M. However, it had no inhibitory action on trypsin, plasmin, kallikrein and thrombin.

EXAMPLE 9 p-Ethoxycarbonylphenyl β-(p-guanidinophenyl)-propionate hydrochloride (Compound No. 47)

Phosphorus pentachloride (22 g) was added to 19.3 g of p-nitrocinnamic acid suspended in 300 ml of ethyl acetate, and the mixture was stirred at room temperature for 1 hour. After the reaction, the solvent was removed by distillation under reduced pressure, upon which p-nitrocinnamoyl chloride precipitated. This was dissolved in 300 ml of ethyl acetate, and 16.6 g of p-ethoxycarbonylphenol was added to the solution, after which 12 g of triethylamine was slowly added at room temperature with stirring. The resulting solution was subjected to reaction at room temperature for 1 hour. Then, 50 ml of 10% HCl was added thereto, and the thus precipitated p-ethoxycarbonylphenyl p-nitrocinnamate was collected by filtration. Yield: 32.3 g (95); melting point: 133°-134° C.; IR (cm$^{-1}$): 1731, 1710. 1517, 1351.

In 200 ml of ethanol were suspended 32.3 g of the p-ethoxycarbonylphenyl p-nitrocinnamate obtained and 2.0 g of 10% palladium-carbon, and gaseous hydrogen was introduced into the resulting suspension with stirring. About 8.5 liters of hydrogen was absorbed in 2 hours. After the reaction, the palladium catalyst was filtered off and the solvent was removed by distillation under reduced pressure. The residue was dissolved in 200 ml of diethyl ether, and gaseous hydrogen chloride was introduced into the solution, upon which p-ethoxycarbonylphenyl β-(p-aminophenyl)-propionate hydrochloride precipitated in the form of colorless crystals. Yield: 28.6 g (87%); melting point: 206-207° C.; IR (Cm$^{-1}$): 3250-2500, 1750, 1710, 1277.

In 200 ml of ethanol were dissolved 28.6 g of the p-ethoxycarbonylphenyl β-(p-aminophenyl)-propionate hydrochloride obtained and 4.2 g of cyanamide, and the solution was subjected to reaction at 70° C. for 5 hours. After the reaction, the solvent was removed by distillation under reduced pressure to obtain an oily product, to which a mixture consisting of ethanol and diethyl ether was added and the solution was cooled, upon which crystals precipitated. The crystals were collected by filtration and recrystallized from an ethanol-diethyl ether mixture to obtain p-ethoxycarbonylphenyl β-(p-guanidinophenyl)propionate hydrochloride in the form of colorless crystals. Yield: 25.1 g (78%); melting point: 125°–127° C.; IR (cm$^{-1}$): 3500–2550, 1750, 1708, 1670, 1599; MS: M$^+$=m/e 355 (M.W. - HCl).

Elementary analysis (as C$_{19}$H$_{22}$N$_3$O$_4$Cl=391.85) Calcd.: C, 58.23%; H, 5.66%; N, 10.72%; Found: C, 57.86%; H, 5.52%; N, 10.49%.

In vitro, this compound inhibited the tosylarginine methyl ester hydrolyzing action of trypsin. The ID$_{50}$ of this compound was 7.8×10$^{-5}$ M. However, it had no inhibitory action on plasmin, kallikrein, Cl esterase and thrombin.

EXAMPLE 10

The compounds shown in Table 2 were synthesized following the above-mentioned procedure, except that starting materials different in R$^1$ and R$^2$ were used.

Table 2

$$\text{[Structure: phenyl ring with } -NH-C(=NH)NH_2 \text{ substituent and } -CH_2-CH(R_1)-COO-R^2 \text{ chain]}$$

| Compound No. | Position of $-NH-C(NH)NH_2$ | $R^1$ | $R^2$ | Salt | Melting point (°C) | Molecular formula | Elementary analysis Calculated (%) C H N | Elementary analysis Found (%) C H N |
|---|---|---|---|---|---|---|---|---|
| 48 | m | H | 4-methylphenyl | HCl | Oil | $C_{17}H_{20}N_3O_2Cl$ | 61.16 6.04 12.59 | 61.32 6.34 12.17 |
| 49 | m | $CH_2CH_3$ | 4-chlorophenyl | $H_2CO_3$ | 95–98 | $C_{19}H_{22}N_3O_5Cl$ | 55.95 5.44 10.30 | 55.66 5.64 10.05 |
| 50 | m | $CH_3$ | naphthyl | HCl | Oil | $C_{21}H_{22}N_3O_2Cl$ | 65.70 5.78 10.95 | 65.01 5.81 10.42 |
| 51 | m | $CH_3$ | chloronaphthyl | HCl | Oil | $C_{21}H_{21}N_3O_2Cl_2$ | 60.29 5.10 10.05 | 59.88 5.60 10.02 |
| 52 | p | $CH_3$ | 4-chlorophenyl | HCl | 148–150 | $C_{17}H_{19}N_3O_2Cl_2$ | 55.44 5.20 11.41 | 55.33 5.00 11.33 |
| 53 | p | $CH_2CH_3$ | 4-chlorophenyl | HCl | Oil | $C_{18}H_{21}N_3O_2Cl_2$ | 56.55 5.54 11.00 | 56.04 5.71 10.66 |
| 54 | p | $CH_3$ | naphthyl | HCl | 116–118 | $C_{21}H_{22}N_3O_2Cl$ | 65.70 5.78 10.95 | 65.80 5.62 10.54 |

Table 2-continued

Structure:

$$\text{HN=C(NH_2)-NH-C_6H_4-CH_2-CH(R_1)-COO-R^2}$$

| Compound No. | Position of -NH-C(=NH)NH₂ | $R^1$ | $R^2$ | Salt | Melting point (°C) | Molecular formula | Calculated (%) C H N | Found (%) C H N |
|---|---|---|---|---|---|---|---|---|
| 55 | p | CH₂CH₃ | naphthyl | HCl | 143–145 | $C_{22}H_{24}N_3O_2Cl$ | 66.40 6.08 10.56 | 66.18 6.31 10.89 |
| 56 | p | CH₂CH₃ | 4-methylphenyl | HCl | Oil | $C_{19}H_{24}N_3O_2Cl$ | 63.18 6.69 11.61 | 63.01 6.90 11.57 |
| 57 | p | CH₂CH₃ | 4-(CH₂COOH)phenyl | H₂CO₃ | 125–127 | $C_{21}H_{25}N_3O_7$ | 58.46 5.84 9.74 | 58.38 5.73 9.44 |
| 58 | p | CH₂CH₃ | 4-(CH₂CH₂COOH)phenyl | H₂CO₃ | 94–95 | $C_{22}H_{27}N_3O_7$ | 59.31 6.11 9.43 | 59.61 6.43 9.59 |
| 59 | m | CH₂CH₃ | naphthyl | HCl | Oil (107–109) | $C_{22}H_{24}N_3O_2Cl$ | 66.40 6.08 10.56 | 66.16 6.56 10.59 |
| 60 | p | CH₂CH₃ | 4-(CH(CH₃)CH₂CH₃)phenyl | CH₃SO₃H | 133–134 (90–92) | $C_{23}H_{33}N_3O_5S$ | 59.59 7.18 9.07 | 59.49 7.20 9.10 |
| 61 | p | CH₂CH₃ | 2,3-dimethylphenyl | CH₃SO₃H | 129–130 | $C_{20}H_{27}N_3O_5S$ | 56.99 6.46 9.97 | 57.00 6.53 9.89 |

Table 2-continued

Structure: Ar-R² with COO-R¹ side chain and guanidino group (-NH-C(=NH)NH₂) on benzene ring

| Compound No. | Position of -NH-C(=NH)NH₂ | R¹ | R² | Salt | Melting point (°C) | Molecular formula | Calculated (%) C | H | N | Found (%) C | H | N |
|---|---|---|---|---|---|---|---|---|---|---|---|---|
| 62 | p | CH₂CH₃ | Br-phenyl | (H₂CO₃) (90-91) | | C₁₉H₂₄N₃O₅BrS | 46.92 | 4.97 | 8.64 | 46.70 | 5.00 | 8.80 |
| | | | | CH₃SO₃H | 82-83 | | | | | | | |
| 63 | m | H | phenyl | H₂CO₃ | 115 | C₁₇H₁₉N₃O₅ | 59.12 | 5.55 | 12.17 | 59.02 | 5.86 | 12.27 |
| 64 | m | H | 4-COOC₂H₅-phenyl | H₂CO₃ | 232-234 | C₂₀H₂₃N₃O₇ | 57.55 | 5.55 | 10.07 | 57.79 | 5.55 | 10.09 |
| 65 | m | CH₂CH₃ | phenyl | H₂CO₃ | 107-108 | C₁₉H₂₃N₃O₅ | 61.11 | 6.21 | 11.25 | 60.90 | 6.46 | 10.75 |
| 66 | m | CH₂CH₃ | 4-COOC₂H₅-phenyl | H₂CO₃ | 65-66 | C₂₂H₂₇N₃O₇ | 59.31 | 6.11 | 9.43 | 58.95 | 5.87 | 9.50 |
| 67 | m | CH₂CH₃ | 4-OCH₃-phenyl | H₂CO₃ | 99-100 | C₂₀H₂₅N₃O₆ | 59.54 | 6.25 | 10.42 | 59.24 | 5.97 | 11.08 |
| 68 | m | CH₂CH₂CH₃ | phenyl | H₂CO₃ | 98-99 | C₂₀H₂₅N₃O₅ | 62.00 | 6.50 | 10.85 | 62.12 | 6.71 | 10.99 |
| 69 | p | H | phenyl | HCl | 158 | C₁₆H₁₈N₃O₂Cl | 60.09 | 5.67 | 13.14 | 59.95 | 5.78 | 13.21 |

Table 2-continued

| Compound No. | Position of -NH-C(NH)NH₂ | R¹ | R² | Salt | Melting point (°C) | Molecular formula | Calculated (%) C H N | Found (%) C H N |
|---|---|---|---|---|---|---|---|---|
| 70 | p | H | ![4-methylphenyl] | HCl | 114–115 | $C_{17}H_{20}N_3O_3Cl$ | 58.36 5.76 12.01 | 58.41 5.89 11.83 |
| 71 | p | H | 4-OCH₃-phenyl / 4-methyl | HCl | 110–115 | $C_{20}H_{26}N_3O_3Cl$ | 61.29 6.69 10.72 | 61.73 6.76 10.85 |
| 72 | p | CH₃ | 4-methylphenyl | H₂CO₃ | 83–87 | $C_{18}H_{21}N_3O_5$ | 60.16 5.89 11.69 | 60.12 5.94 12.01 |
| 73 | p | CH₂CH₃ | 4-methylphenyl | H₂CO₃ | 100–101 | $C_{19}H_{23}N_3O_5$ | 61.11 6.21 11.25 | 60.91 6.31 11.26 |
| 74 | p | CH₂CH₃ | 4-methylphenyl | CH₃SO₃H | 117–119 | $C_{19}H_{25}N_3O_5S$ | 56.00 6.18 10.31 | 55.41 6.19 10.33 |
| 75 | p | CH₂CH₃ | 4-methylphenyl | H₃C-C₆H₄-SO₃H | 118–121 (sinter) | $C_{25}H_{29}N_3O_5S$ | 62.09 6.05 8.69 | 62.13 5.99 8.73 |
| 76 | p | CH₂CH₃ | 4-COOC₂H₅-phenyl | H₂CO₃ | 100–102 | $C_{22}H_{27}N_3O_7$ | 59.31 6.11 9.43 | 59.14 5.89 9.42 |
| 77 | p | CH₃ | 4-COOC₂H₅-phenyl | H₂CO₃ | 55–58 | $C_{21}H_{25}N_3O_7$ | 58.46 5.84 9.74 | 58.30 5.74 9.80 |

Table 2-continued

Structure:

$$\underset{NH}{\overset{NH}{\underset{\|}{C}}}-NH-\underset{}{\text{C}_6\text{H}_4}-CH_2-CH(R_1)-COO-R^2$$

| Compound No. | Position of amidino group | R¹ | R² | Salt | Melting point (°C.) | Molecular formula | Elementary analysis Calculated (%) C H N | Elementary analysis Found (%) C H N |
|---|---|---|---|---|---|---|---|---|
| 78 | p | CH₃ | –C₆H₄–OCH₃ (p) | HCl | Oil | C₁₈H₂₂N₃O₃Cl | 59.42 6.10 11.55 | 59.37 6.00 11.85 |
| 79 | p | CH₂CH₃ | –C₆H₄–COO(CH₂)₃CH₃ | CH₃SO₃H | 79–78 (101–103) | C₂₄H₃₃N₃O₇S | 56.79 6.55 8.28 | 56.80 6.71 8.30 |
| 80 | p | CH₂CH₃ | –C₆H₄–COOCH₃ | CH₃SO₃H (99–100) | 113–114 | C₂₁H₂₇N₃O₇S | 54.18 5.85 9.03 | 54.30 5.55 8.99 |
| 81 | p | CH₂CH₃ | –C₆H₄–OCH₃ (m) | CH₃SO₃H (H₂CO₃) | 124–125 (98–99) | C₂₀H₂₇N₃O₆S | 54.90 6.22 9.61 | 55.01 6.09 9.50 |
| 82 | p | CH₂CH₃ | –C₆H₄–OCH₃ (p) | CH₃SO₃H | 125–126 | C₂₀H₂₇O₆N₃S | 54.90 6.22 9.61 | 54.77 6.13 9.57 |

Application Example (A) Determination of Enzyme-inhibitory Activity:
The enzyme-inhibitory activities in vitro of the compounds of this invention were measured by the following procedure according to the method of M. Muramatsu et al. [M. Muramatsu, T. Onishi, S. Makino, Y. Hayashi and S. Fujii: J. Biochem., 58, 214 (1965)].

(1) Inhibitory Effect on Ester-hydrolyzing Activity of Trypsin

To 0.1 ml of trypsin (5 μg/ml) were added 0.5 ml of 0.1 M borate buffer solution (pH 8.6) containing 10 mM $CaCl_2$, and 0.1 ml of a varying concentration of an inhibitor solution, and preincubation was carried out at 37° C. for 5 minutes. Then, 10 μmoles of the substrate, TAMe (tosylarginine methyl ester), was added, and incubation was performed at 37° C. for 30 minutes.

After the incubation, 1.5 ml of 2 M alkaline hydroxylamine was added and thoroughly mixed, and allowed to stand at room temperature for 15 minutes. Then, 1.0 ml of each of 18% trichloroacetic acid, 4 N HCl and 10% $FeCl_3$ was added and thoroughly mixed. If necessary, the mixture was centrifuged at 3,000 rpm for 10 minutes, and the absorbance of the supernatant was measured at 530 nm.

(2) Inhibitory Effect on Ester-hydrolyzing Activity of Human Plasmin

It was measured by using 0.1 ml of plasmin (generated by activation of plasminogen with streptokinase) and TAMe as substrate following the method described in (1).

(3) Inhibitory Effect on Ester-Hydrolyzing Activity of Human Plasma Kallikrein

It was measured by using 0.5 ml of kallikrein, (generated by activation of kallikreinogen with acetone), and TAMe as substrate following the method described in (1).

(4) Inhibitory Effect on Ester-Hydrolyzing Activity of Bovine Thrombin

It was measured by using 0.4 ml of bovine thrombin (1 μ/ml), 0.02 M sodium phosphate buffer solution (pH 7.4) and TAMe as substrate following the method described in (1).

(5) Inhibitory Effect on Ester-Hydrolyzing Activity of Human C1 Esterase [K. Okamura, M. Muramatsu, and S. Fujii: Biochem. Biophys. Acta, 295 252-257 (1973)].

It was measured by using 0.1 ml of C1 esterase, 0.1 ml of 0.02 M sodium phosphate buffer solution (pH 7.4) and 10 μmoles of ATEe (acetyltyrosine ethyl ester) as substrate following the method described in (1).

Enzyme-inhibitory activities (percent inhibition at $10^{-3}$M or $ID_{50}$) of the compounds are shown in Table 3.

Table 3

| Compound No. | R | $R^1$ | $R^2$ | Trypsin | Plasmin | Esterase C1 | Kallikrein | Thrombin |
|---|---|---|---|---|---|---|---|---|
| 1 | p-$NH_2$ | H | –⟨O⟩–Me | NE | NE | NE | NE | [$8.8 \times 10^{-4}$] |
| 3 | p-$NH_2$ | H | –⟨O⟩ | NE | NE | NE | NE | [$2.9 \times 10^{-4}$] |
| 4 | m-$NH_2$ | Et | –⟨O⟩–OMe | [$4.0 \times 10^{-4}$] | NE | 14.8 | NE | NE |
| 5 | m-$NH_2$ | Me | –⟨O⟩–Cl | [$1.0 \times 10^{-5}$] | NE | NE | NE | NE |
| 7 | m-$NH_2$ | Et | –⟨O⟩–⟨O⟩ | [$1.0 \times 10^{-5}$] | NE | 11.7 | — | NE |
| 32 | p-$NH_2$ | H | –⟨O⟩–OMe | 38.8 | NE | NE | NE | [$1.7 \times 10^{-4}$] |

Table 3-continued

[structure: phenyl-CH2-CH(R1)-COOR2 with R on ring]

| Compound No. | R | R¹ | R² | Trypsin | Plasmin | Esterase Cl | Kallikrein | Thrombin |
|---|---|---|---|---|---|---|---|---|
| 33 | p-NH$_2$ | H | —⟨⟩—OBu | [$8.9 \times 10^{-4}$] | NE | NE | NE | 19.9 |
| 36 | p-NH$_2$ | Et | —⟨⟩—COOEt | [$1.7 \times 10^{-4}$] | NE | NE | 15.9 | 25.3 |
| 45 | p-G | Me | —⟨⟩—Me | 21.4 | NE | [$7.8 \times 10^{-4}$] | NE | NE |
| 46 | m-G | Me | —⟨⟩ | 12.2 | NE | [$3.1 \times 10^{-4}$] | 12.9 | NE |
| 47 | p-G | H | —⟨⟩—COOEt | [$7.8 \times 10^{-5}$] | NE | NE | 36.0 | 12.3 |
| 50 | m-G | Me | —⟨⟩⟨⟩ | [$5.7 \times 10^{-5}$] | 42.0 | [$1.4 \times 10^{-4}$] | — | NE |
| 52 | p-G | Me | —⟨⟩—Cl | [$4.9 \times 10^{-4}$] | 18.8 | [$5.6 \times 10^{-5}$] | 38.4 | NE |
| 65 | m-G | Et | —⟨⟩ | 35.0 | NE | [$7.0 \times 10^{-5}$] | 15.6 | 16.8 |
| 68 | m-G | Pr | —⟨⟩ | NE | 22.0 | [$4.3 \times 10^{-4}$] | 17.6 | NE |
| 71 | p-G | H | —⟨⟩—OBu | [$6.6 \times 10^{-4}$] | 20.0 | NE | 1.5 | NE |
| 73 | p-G | Et | —⟨⟩ | 43.9 | NE | [$3.1 \times 10^{-4}$] | 31.5 | NE |

Note:

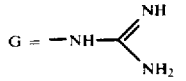

Bu = —CH$_2$CH$_2$CH$_2$CH$_3$
Pr = —CH$_2$CH$_2$CH$_3$
Et = —CH$_2$CH$_3$
Me = —CH$_3$
NE = Not effective
[ ] $ID_{50}$ (M)

(B) Determination of Inhibitory Activity on Collagen Induced Platelet Aggregation:

According to the method of Born et al. [Born, G. V. R.: J. Physiol., 168. 178 (1963)], the platelet aggregation inhibition (%) was determined at various concentrations of compounds by the following procedure:

Rabbit PRP (platelet rich plasma), 0.9 ml, obtained from sodium citrate-added blood, was taken into a polyethylene tube and incubated at 37° C. for 1 minute, and then 10 μl of a compound solution or physiological saline as control, was added.

Subsequently, 0.1 ml of collagen solution was added, and change in absorbance of PRP, resulting from the progress of platelet aggregation, was determined by means of platelet aggregation meter and recorded.

Percent inhibition was calculated according to the following equation:

$$\text{Percent inhibition} = \frac{\begin{bmatrix}\text{Maximum absorbance} \\ \text{change} \\ \text{(PRP + inducer)}\end{bmatrix} - \begin{bmatrix}\text{Maximum absorbance} \\ \text{change (PRP +} \\ \text{compound + inducer)}\end{bmatrix}}{\text{Maximum absorbance change (PRP + inducer)}} \times 100$$

The results are shown in Table 4.

Table 4

| Compound No. | Inhibition of collagen induced platelet aggregation of rabbit PRP Concentration of compound (μg/ml) | | | | |
|---|---|---|---|---|---|
| | 0.5 | 1.0 | 2.5 | 5.0 | 10.0 |
| 50 | — | 4% | 100% | 100% | 100% |
| 7 | — | — | 37% | 84% | 100% |
| 32 | — | — | 41% | 100% | 100% |
| 1 | — | — | — | — | 42% |
| 33 | 46% | 100% | 100% | 100% | 100% |
| aspirin | — | — | — | 78% | 100% |

(C) Determination of Antihemolytic Activity: Preventions of the complement-dependent hemolysis by the compounds of this invention were measured according to the method of B. R. Baker et al. [J. Med. Chem., 12, 408–414 (1969)] by the following procedure:

In a test tube were placed 0.5 ml of sensitized erythrocytes ($5 \times 10^8$ cells/ml), 0.1 ml of a sample solution (final $10^{-3}$ or $10^{-4}$ M) and 0.4 ml of complement (1:140) in this order. The mixture was incubated at 37° C. for 10 minutes. The reaction was stopped by adding 2.7 ml of an ice-cold citrate-saline solution, and the resulting mixture was centrifuged at 3000 rpm for 3 minutes. Absorbance of the supernatant was measured at 541 nm. As the standard, $GVB^{2+}$ (gelatin veronal buffer) was substituted for the sample solution and, as the control, $GVB^{2+}$ was substituted for the complement.

The antihemolytic activity of each compound was calculated, taking the absorbance of the standard as 100%. The results are shown in Table 5.

Table 5

| Compound No. | Inhibition (%) | |
|---|---|---|
| | $10^{-3}$ M. | $10^{-4}$ M. |
| 73 | 69.1 | 30.0 |
| 76 | | 33.0 |
| 54 | | 49.3 |
| 68 | | 30.0 |

(D) Effect on Masugi Nephritis: The effect of Compound No. 73 on Masugi nephritis was investigated according to the method of Shibata et al. [S. Shibata: Men-ekigaku, Arerugi-gaku Jikkenho (Immunology, Experimental Methods in Allergology), p. 664, (1971), Bunkodo, Tokyo].

Male sprague-Dawley rats weighing about 200 g were divided into normal group, diseased group and treated group, each consisting of 7 rats. For the purpose of inducing nephritis, 0.5 ml of anti- "rat nephritis" rabbit serum, which had been prepared according to the method of Shibata et al., was administered intravenously to rats of both diseased and treated groups. To the normal group was intravenously administered the same quantity of physiological saline.

The test drug was administered intraperitoneally to rats of the treated group three times, namely two days prior to, one day prior to and on the day of administration of the antiserum. From the rats of each group, a 24 hours urine specimen was collected on the day preceding, and the 1st, 2nd, 5th, 8th and 13th days following the administration of the antiserum. Protein contents of the urine specimen were determined by the sulfosalicylic acid method. The results obtained are shown in Table 6.

The acute toxicity of Compound No. 73 by the intraperitoneal administration in mice was found to be 129 mg/kg in $DL_{50}$ value.

Table 6

Effect of Compound No. 73 on Rat Masugi Nephritis

| Dose mg/kg | Days after antiserum i.v. (Protein mg/day) Day | | | | | |
|---|---|---|---|---|---|---|
| | −1 | 1 | 2 | 5 | 8 | 13 |
| Normal | 5.7 | 8.3 | 14.4 | 12.7 | 14.9 | 11.9 |
| 0 | 8.2 | 67.9 | 66.5 | 78.2 | 126.3 | 127.5 |
| 12.5 | 6.0 | 34.0 | 42.5 | 45.6 | 76.3 | 115.5 |
| 25.0 | 4.2 | 41.1 | 33.9 | 39.4 | 63.3 | 71.5 |

What is claimed is:

1. An amino- or guanidino-phenylpropionic ester compound represented by formula (I):

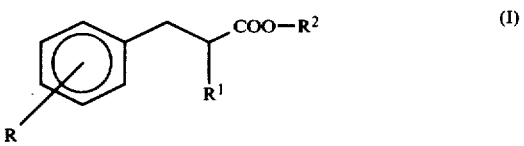

wherein R is in meta or para position and is $-NH_2$ or

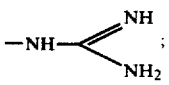

$R^1$ is hydrogen or a lower alkyl group; $R^2$ is an unsubstituted $NH_2$ or a lower-alkyl-, carboxyalkyl- in which the alkyl group is $C_1$ or $C_2$ alkyl, lower-alkoxy-, lower-alkoxycarbonyl- or halogen-substituted phenyl group or an unsubstituted or a halogen-substituted naphthyl group, or a pharmaceutically acceptable acid addition salt thereof.

2. An amino-phenylpropionic ester compound or a pharmaceutically acceptable acid addition salt thereof according to claim 1, wherein R in formula (I) is $-NH_2$.

3. A guanidinophenylpropionic ester compound or a pharmaceutically acceptable acid addition salt thereof according to claim 1, wherein R in formula (I) is

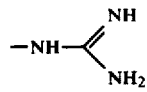

4. An amino- or guanidino-phenylpropionic ester compound or a pharmaceutically acceptable acid addition salt thereof according to claims 1, 2 or 3, wherein $R^2$ in formula (I) is phenyl, lower-alkoxy-substituted phenyl or lower-alkoxycarbonyl-substituted phenyl.

5. An amino- or guanidino-phenylpropionic ester compound or a pharmaceutically acceptable acid addition salt thereof according to claim 4, wherein $R^1$ in formula (I) is hydrogen, methyl, ethyl, n-propyl or n-butyl.

6. An amino- or guanidino-phenylpropionic ester compound or a pharmaceutically acceptable acid addition salt thereof according to claim 4, wherein $R^1$ in formula (I) is hydrogen.

7. An amino- or guanidino-phenylpropionic ester compound or a pharmaceutically acceptable acid addition salt thereof according to claim 4, wherein $R^1$ in formula (I) is methyl, ethyl, n-propyl or n-butyl.

8. An amino- or guanidino-phenylpropionic ester compound or a pharmaceutically acceptable acid addition salt thereof according to claim 4, wherein said lower alkoxy and lower alkoxy-carbonyl are $C_{1-4}$ alkoxy and $C_{1-4}$ alkoxy-carbonyl, respectively.

9. An amino- or guanidino-phenylpropionic ester compound or a pharmaceutically acceptable acid addition salt thereof according to claim 1, 2 or 3 wherein $R^1$ is hydrogen, methyl, ethyl or n-propyl and $R^2$ is phenyl, methoxyphenyl, n-butoxyphenyl or ethoxycarbonylphenyl.

10. A pharmaceutically acceptable acid addition salt of an amino- or guanidino-phenylpropionic ester compound according to claim 9 wherein said acid addition salt is a hydrochloride, carbonate, methane-sulfonate or tosylate.

11. An amino- or guanidino-phenylpropionic ester compound or a pharmaceutically acceptable acid addition salt thereof according to claim 1, 2 or 3, wherein $R^2$ in formula (I) is said lower-alkyl-, carboxyalkyl- or halogen-substituted phenyl or an unsubstituted or a halogen-substituted naphthyl.

12. An amino- or guanidino-phenylpropionic ester compound or a pharmaceutically acceptable acid addition salt thereof according to claim 11, wherein the lower alkyl substituent has 1 to 4 carbon atoms and the alkyl group of the carboxyalkyl substituent has 1 to 2 carbon atoms, and the halogen substituent is chlorine or bromine.

13. An amino- or guanidino-phenylpropionic ester compound or a pharmaceutically acceptable acid addition salt thereof according to claim 11, wherein $R^1$ is hydrogen, methyl, ethyl, n-propyl or n-butyl.

14. An amino- or guanidino-phenylpropionic ester compound or a pharmaceutically acceptable acid addition salt thereof according to claim 11, wherein $R^1$ in formula (I) is hydrogen.

15. An amino- or guanidino-phenylpropionic ester compound or a pharmaceutically acceptable acid addition salt thereof according to claim 11, wherein $R^1$ in formula (I) is methyl or ethyl.

16. An amino- or guanidino-phenylpropionic ester compound or a pharmaceutically acceptable acid addition salt thereof according to claim 1, 2 or 3, wherein $R^1$ in formula (I) is hydrogen, methyl or ethyl and $R^2$ is monochlorophenyl, monobromophenyl, monomethylphenyl, dimethylphenyl, carboxymethylphenyl, carboxyethylphenyl, naphthyl or monochloronaphthyl.

17. A pharmaceutically acceptable acid addition salt of an amino- or guanidino-phenylpropionic ester compound according to claim 16, wherein said acid addition salt is a hydrochloride, carbonate, methanesulfonate or tosylate.

18. p-Methylphenyl β-(p-aminophenyl)-propionate or its hydrochloride.

19. p-Chlorophenyl α-methyl-β-(m-aminophenyl)-propionate or its hydrochloride.

20. Phenyl β-(p-aminophenyl)-propionate or its hydrochloride.

21. Naphthyl α-ethyl-β-(m-aminophenyl)-propionate or its hydrochloride.

22. Phenyl α-ethyl-β-(p-guanidinophenyl)-propionate or its carbonate, methanesulfonate or tosylate.

23. p-Ethoxycarbonylphenyl α-ethyl-β-(p-guanidinophenyl)-propionate or its hydrochloride.

24. 1-Naphthyl α-methyl-β-(p-guanidinophenyl)-propionate or its carbonate.

25. p-Ethoxycarbonylphenyl β-(p-guanidinophenyl)-propionate or its hydrochloride.

26. Phenyl α-propyl-β-(m-guanidinophenyl)-propionate or its carbonate.

27. p-Chlorophenyl α-ethyl-β-(p-guanidinophenyl)-propionate or its hydrochloride.

28. o-Bromophenyl α-ethyl-β-(p-guanidinophenyl)-propionate or its carbonate or methanesulfonate.

29. m-Methoxyphenyl α-ethyl-β-(p-guanidinophenyl)propionate or its carbonate or methanesulfonate.

30. m-Methoxycarbonylphenyl α-ethyl-β-(p-guanidinophenyl)-propionate or its carbonate or methanesulfonate.

* * * * *